US00PP11508P

United States Patent [19]

Kudo

[11] Patent Number: Plant 11,508

[45] Date of Patent: Sep. 12, 2000

[54] APPLE TREE VARIETY NAMED 'KANKI'

[75] Inventor: Seiichi Kudo, Hirosaki, Japan

[73] Assignee: Fuminobu Saito, Hirosaki, Japan

[21] Appl. No.: 08/747,284

[22] Filed: Nov. 12, 1996

[51] Int. Cl.[7] ..... A01H 5/00

[52] U.S. Cl. ..... Plt./161

[58] Field of Search ..... Plt./34.1, 161, Plt./168

[56] References Cited

PUBLICATIONS

UPOV–ROM, Jan. 1998, Plant Variety Database, GTI Jouve Retrieval Software. Citation for 'Kanki'.

*Primary Examiner*—Howard J. Locker
*Attorney, Agent, or Firm*—Armstrong, Westerman, Hattori, McLeland & Naughton

[57] ABSTRACT

A mid-season apple tree variety bearing fruit with a yellow ground color and bright red overcolor overall, and a medium flesh which is very juicy, moderately sweet and with low acidity.

5 Drawing Sheets

The present invention relates to a new and distinct variety of apple tree which is a mid-season variety exhibiting less fruit drop and less cracking than the 'SENSHU' variety, and producing a dessert apple which is less acid than 'SENSHU'.

This new and distinct cultivar was bred by Seiichi Kudo in search of a variety which does not have the less desirable characteristics of the 'SENSHU' variety. He crossed 'SENSHU' with 'TSUGARU' in 1981. The following spring he seeded one hundred seeds of the cross and developed one hundred seedlings in his orchard (at No. 63, aza Izumida, Ooaza Ishikawa, Hirosaki City, Aomori prefecture, Japan). In 1988 he gathered the first crop from the seedlings. He selected one tree which produced fruit of excellent eating quality and few defects, less fruit cracking and less fruit drop. For confirmation of the stability of the characteristics of the seedling, he grafted the budwoods on other trees in 1989 in his orchard at the same location. Continued observation of the seedlings indicated that the characteristics of the variety of the invention were stable, and were transmitted without change through succeeding propagation.

BRIEF DESCRIPTION OF THE DRAWINGS

The accompanying photographic illustrations show typical specimens of the foliage and fruit of the new variety. The colors depicted are as true as is reasonably possible to attain in color illustrations of this character.

DETAILED DESCRIPTION OF VARIETY

Figure 1:
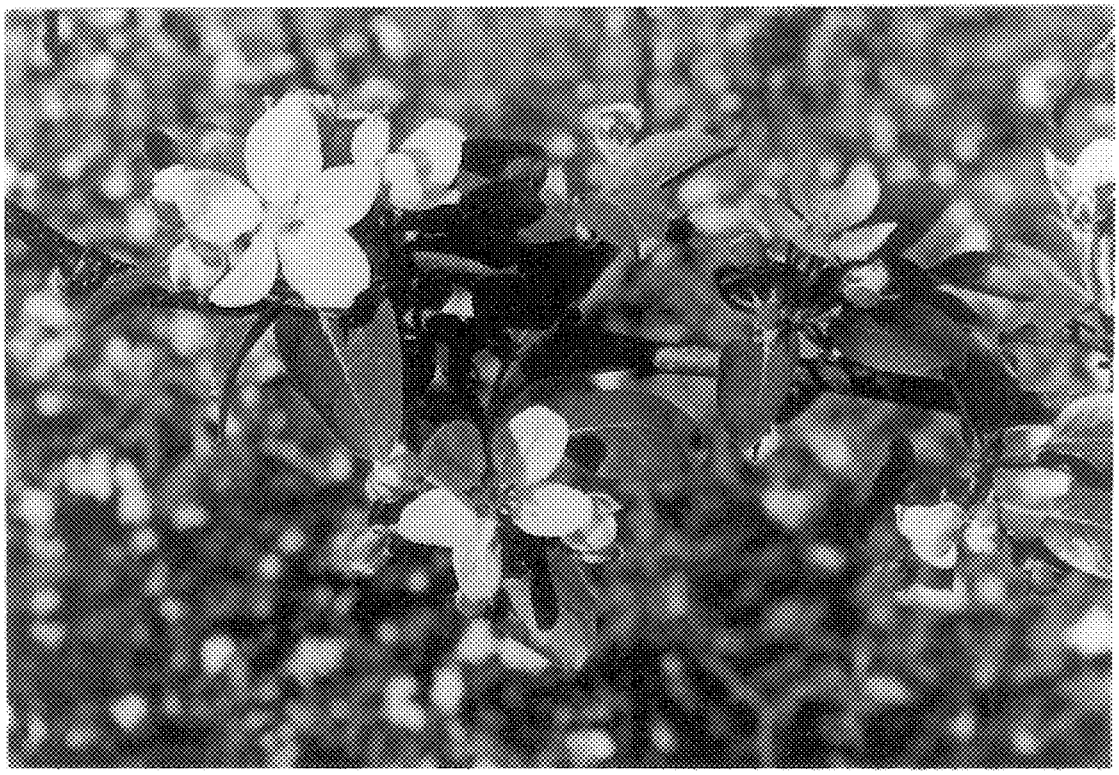
FIG. 1 is a photograph illustrating buds, opened flowers, foliage and stem characteristics of the plant.
Figure 2:
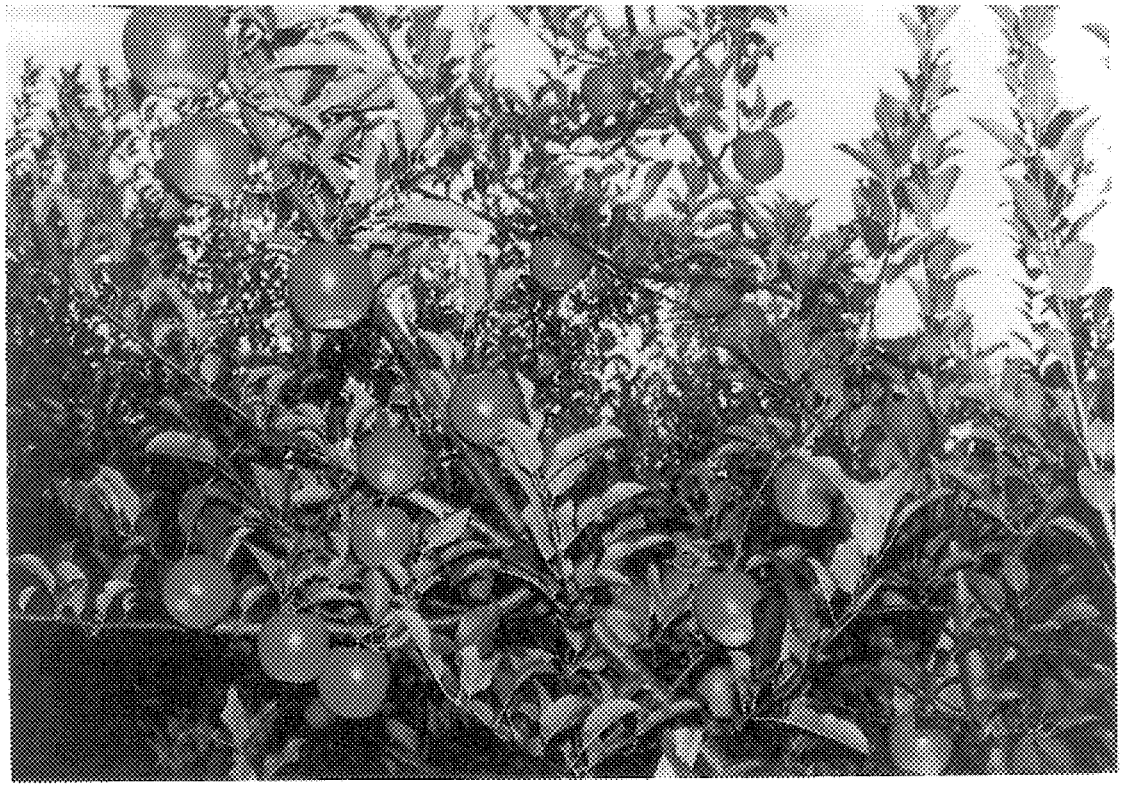
FIG. 2 is a photograph showing typical bearing characteristics of the plant, along with fruit, foliage, and stem coloration of same.
Figure 3:
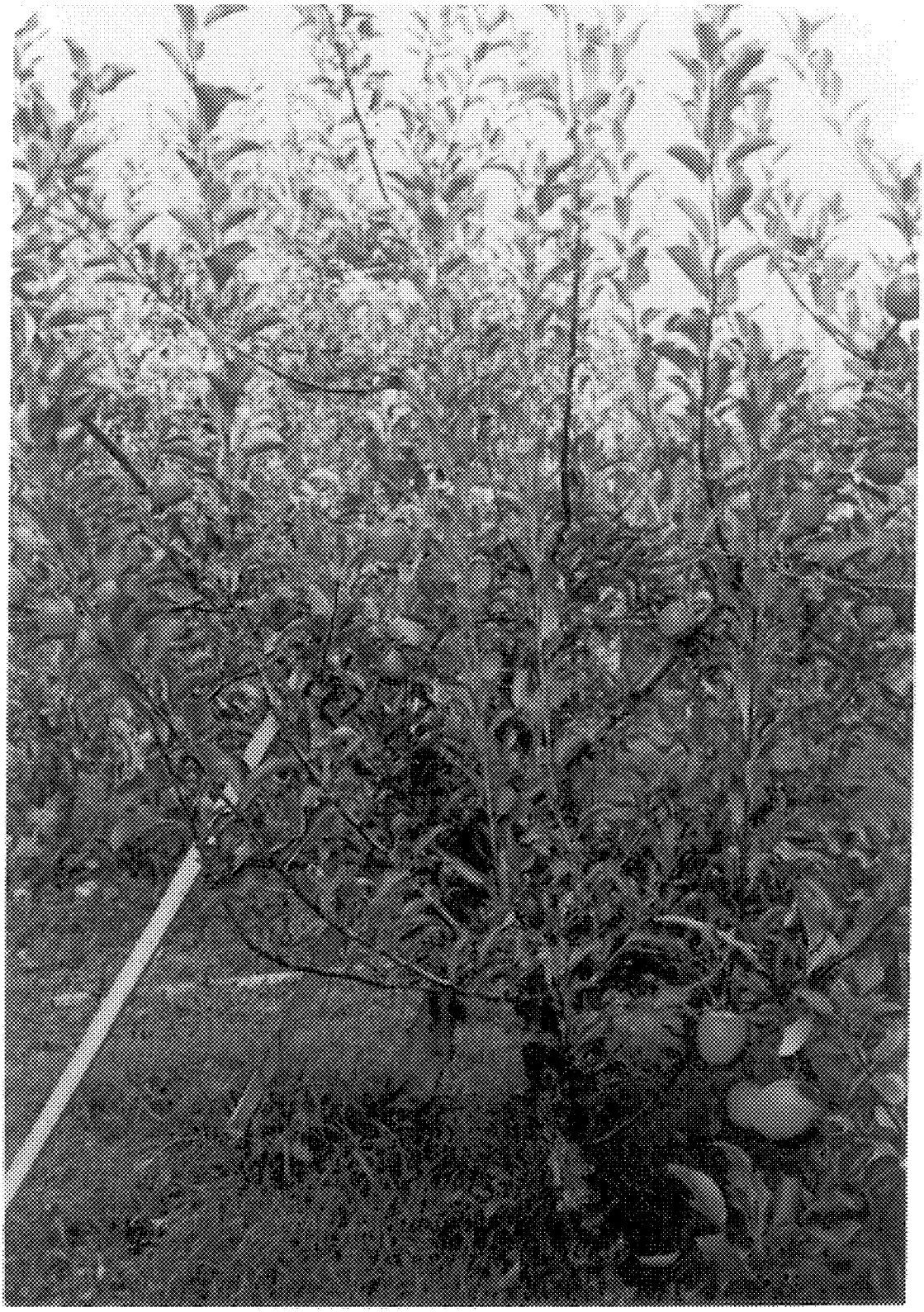
FIG. 3 is a whole plant view.
Figure 4:
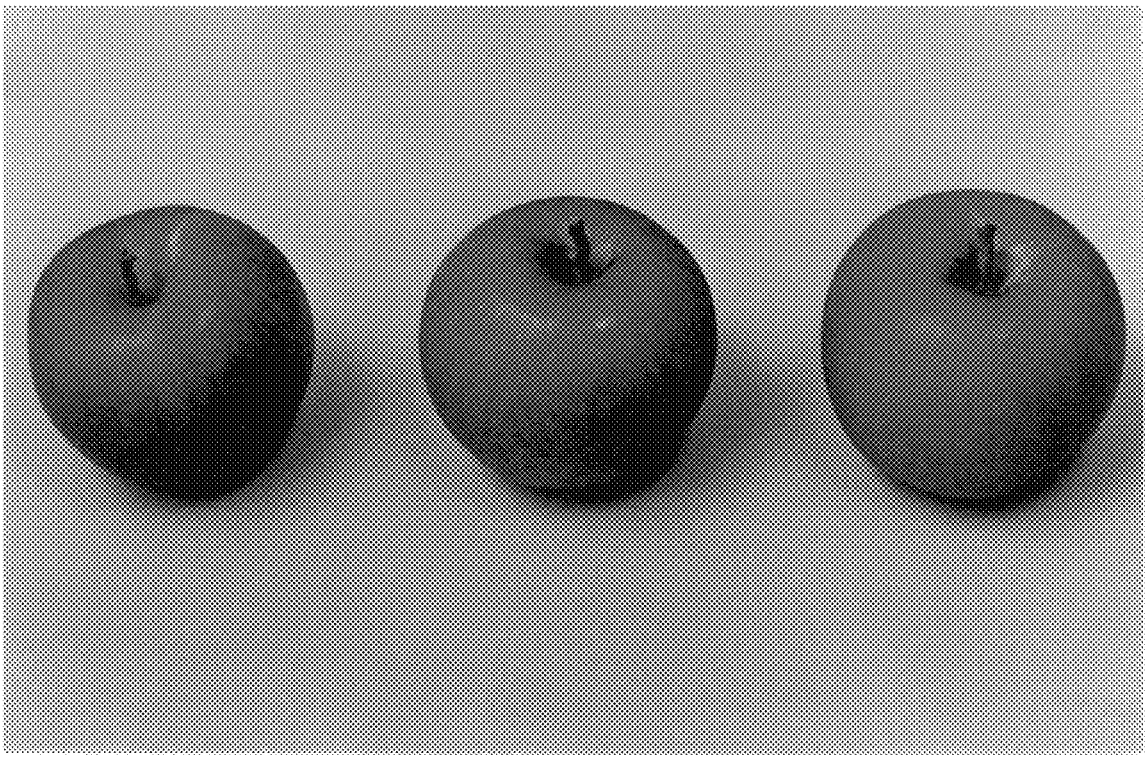
FIG. 4 is a photograph of typical 'KANKI' fruit.
Figure 5:
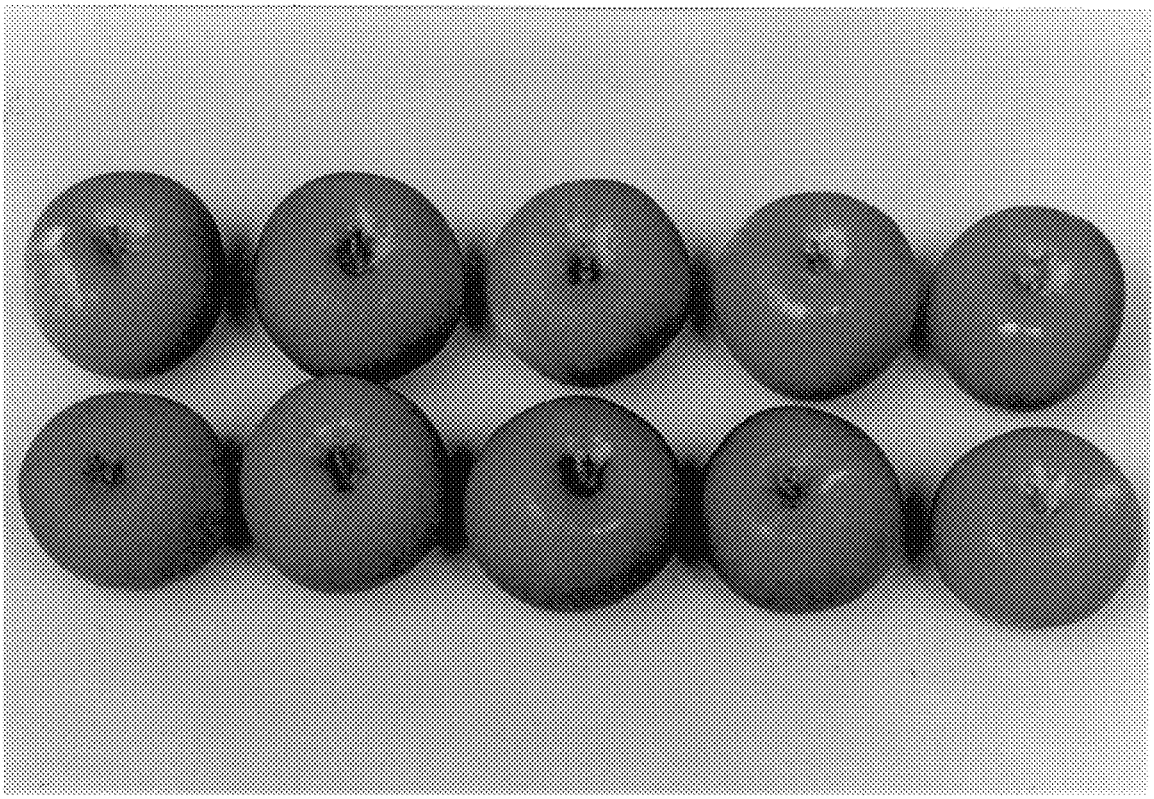
FIG. 5 is a photograph of 'KANKI' fruit as viewed from the stalk cavity.
Figure 6:
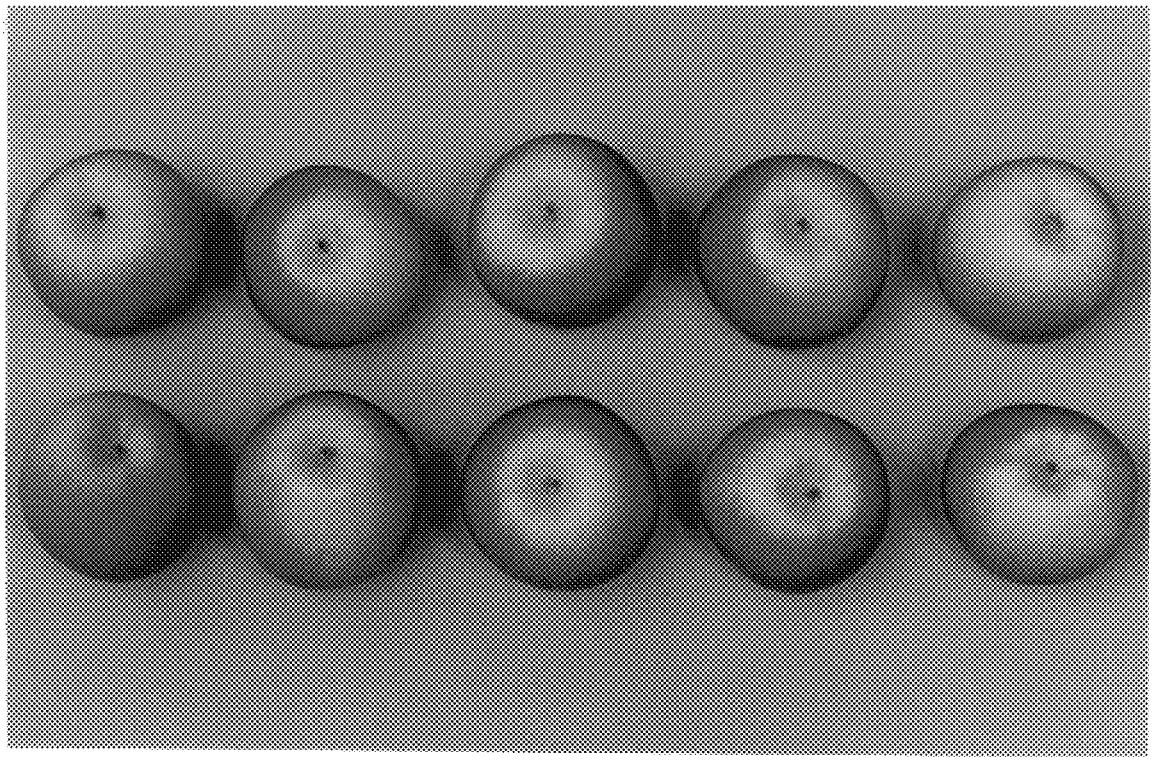
FIG. 6 is a photograph of 'KANKI' fruit as viewed from the base.
Figure 7:
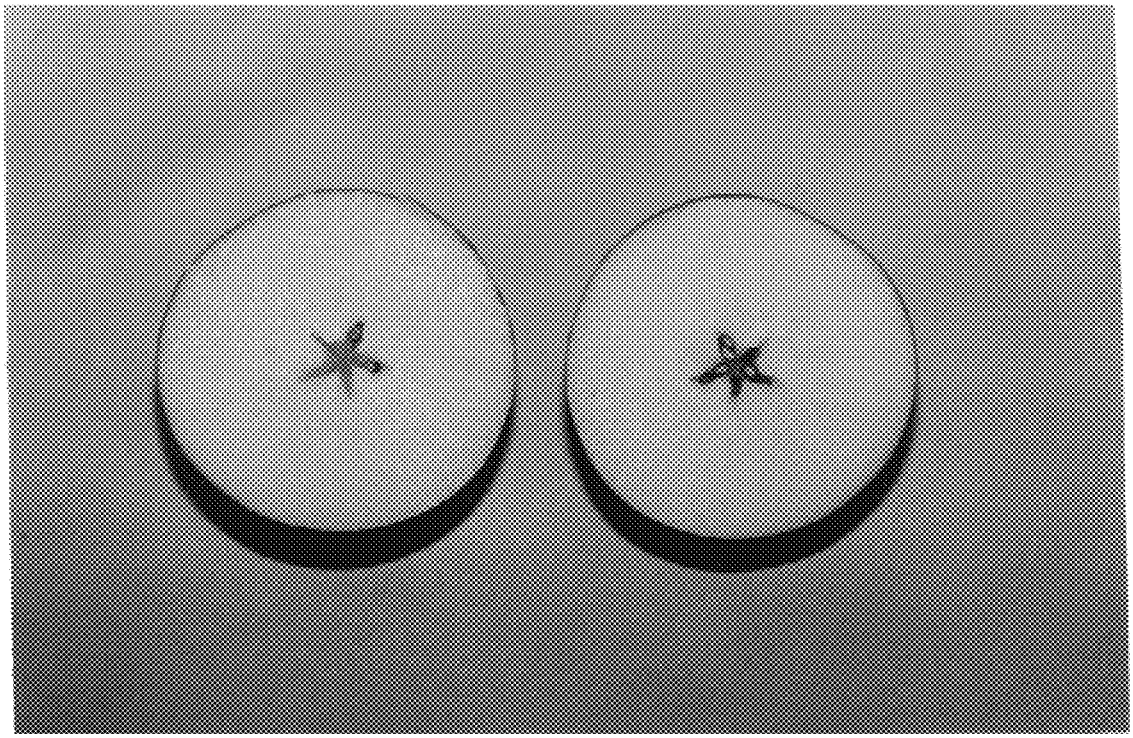
FIG. 7 shows the fruit in cross-section.
Figure 8:
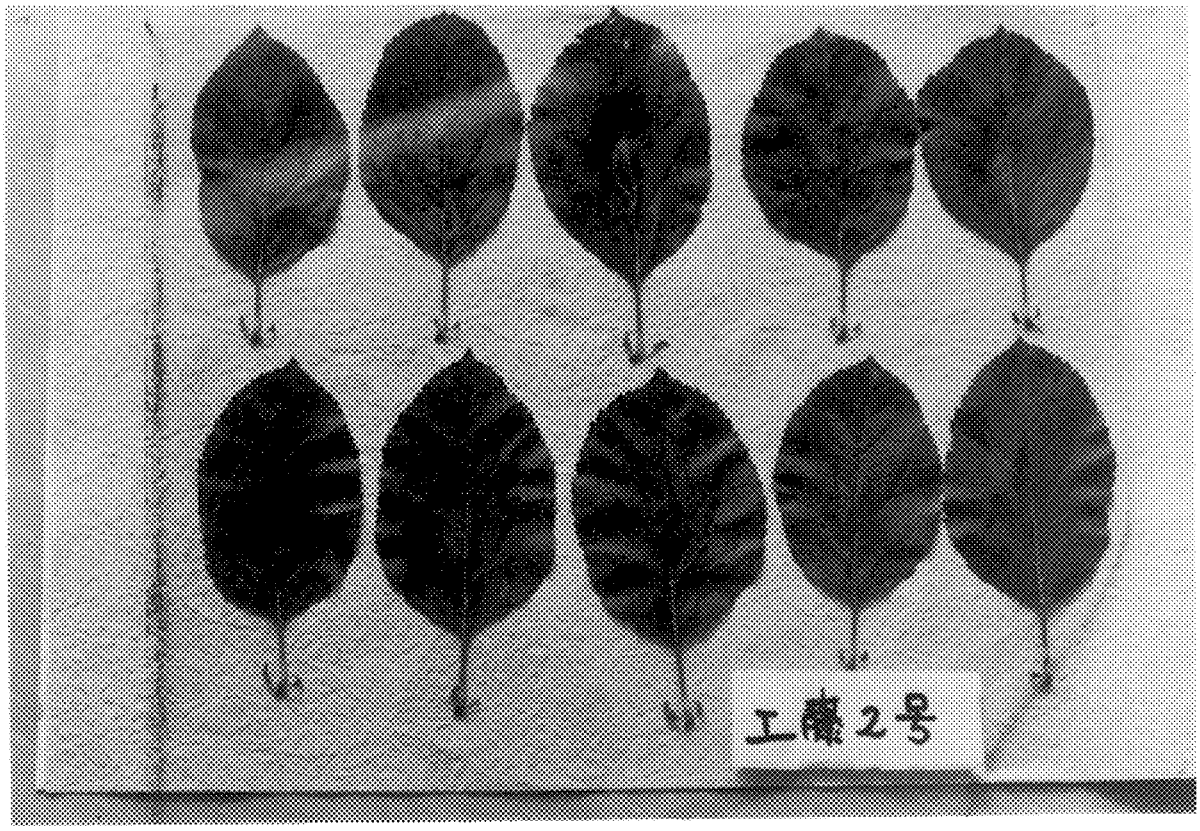
FIG. 8 is a photograph of the foliage, including petiole and stipules.

The characteristics of the new variety 'KANKI' are as follows, with color description provided according to the Munsell Color Chart.

Botanical name: '*Malus domestica*'.

Tree: The tree is precocious and vigorous, of medium size, tending to be bigger than 'MIKI LIFE' but smaller than 'FUJI', with spreading habit and production of many lateral shoots and spurs. The branch density tends to be less than that for 'FUJI' and higher than for 'TSUGARU' and 'JONATHAN'. The angle of branches is as wide as for 'FUJI'; wider than for 'OURIN', but narrower than for 'JONATHAN', 'JONAGOLD', 'TSUGARU' and 'MUTSU'. 'KANKI' tends to have more shoots than 'FUJI'. 'KANKI' has stronger branches than 'TSUGARU', and tends to have fewer shoots than 'TSUGARU'. The fruit of 'KANKI' is smaller and more acid than the fruit of 'TSUGARU'. Chemical treatment to prevent fruit fall is necessary for 'KANKI' just as for 'TSUGARU'. Light thinning is preferable for cultivation of 'KANKI'. Inducing lateral branches is necessary for dense cultivation, whereas keeping long branches results in less fruit bearing branches. Branches having wide angles should be selected for cultivation, with short fruit branches and medium fruit branches being preferred. Production of lateral flower buds is limited.

Shoot: The shoot is of medium thickness and the internode is of medium length (2.81 cm).

Leaves: The leaf is of medium size, the length/width ratio of the leaf blade being medium. The leaf margin is wavy with crenate serrations. The length of the leaf blade is 10.47 cm, the width is 7.31 cm, the petiole is long (3.40 cm) and thick (0.21 cm). The base of the petiole coloring reaches up to the center of the costa (main vein) of the reverse side of the leaf. The leaf color is dark green (Munsell 7GY3/5). The color of the reverse side of the leaf is dark yellow green. The stipule is elongated, with a length of 0.57 cm.

Flower: The flower is larger than in 'SENSHU' with a diameter of 4.59 cm. The unopened flower is of a strong purplish color (Munsell 2RP6/12.5). The time of flowering is midseason. Blooming starts around May 10, full bloom being around May 15, and flowers falling around May 18. 'KANKI' is not self-fertile. Fruit thinning is required for inducing annual (versus biannual) bearing and obtaining the disclosed fruit size. The fruits on the center of short, medium and long branches are kept. Picking one fruit in four terminal buds as for 'FUJI' is appropriate.

Fruit:

*Shape.*—The fruit is of medium size (approximately 293.3 g, 7.7 cm in diameter), which is almost the same as for 'FUJI', and is conical with crowning. The aperture of the eye is closed. The base cavity and the stalk cavity are of medium depth and breadth, more shallow and wider than in 'SENSHU'. The stalk (2.1 cm) is longer than in 'SENSHU', and of medium thickness without distinct swelling at the end.

*Flesh.*—The flesh is yellowish white, very juicy with moderately sweet taste (Brix 13.4) and low acidity (acid 0.342 g/100 ml). The flavor is medium. The firmness is medium, and the texture of the fruit is medium. Browning is very heavy. The mature fruit has no water core.

*Skin.*—Ground color is yellow. The over color of the skin is bright red which covers the base color. Before maturity when the coloring is light, stripes are clearly visible. After full coloring the stripes become less distinct. the base color remains around the base of the stalk around the stalk cavity. The base color also remains around the calyx. The skin has medium small lenticels of medium density, has a scarf skin, is moderately shiny, with low greasiness, and is smooth without bloom. There is no cracking tendency of the skin.

*Core.*—Conical and small in size.

*Seed.*—Seeds are numerous and obovate, of medium size.

Resistance: 'KANKI' has good resistance to powdery mildew and Alternaria blotch, and has no or little tendency for moldy carpels.

Harvest season: September 25–October 5, which is 7–10 days ahead of 'SENSHU'. The time between blooming and harvest is about 139 to 149 days.

Storability: Moderate.

Use: 'KANKI' is a good variety of dessert apple.

I claim:

1. A new and distinct mid-season variety of apple tree named 'KANKI', substantially as illustrated and described herein, bearing fruit with a yellow ground color and bright red overcolor overall, and a medium flesh which is very juicy, moderately sweet and with low acidity.

* * * * *